US012765989B2

(12) United States Patent
LeBlanc et al.

(10) Patent No.: US 12,765,989 B2
(45) Date of Patent: Oct. 20, 2026

(54) COMPRESSION SYSTEM CONFIGURED TO EMBED GRAFT INTO SURGICAL IMPLANT AND CORRESPONDING METHOD

(71) Applicant: Arthrex, Inc., Naples, FL (US)

(72) Inventors: Shaun LeBlanc, Naples, FL (US); Thomas Dooney, Jr., Naples, FL (US); Paul C. Brady, Knocksville, TN (US)

(73) Assignee: ARTHREX, INC., Naples, FL (US)

( * ) Notice: Subject to any disclaimer, the term of this patent is extended or adjusted under 35 U.S.C. 154(b) by 423 days.

(21) Appl. No.: 18/529,187

(22) Filed: Dec. 5, 2023

(65) Prior Publication Data

US 2025/0177117 A1 Jun. 5, 2025

(51) Int. Cl.

| | |
|---|---|
| ***A61F 2/08*** | (2006.01) |
| ***A61B 17/00*** | (2006.01) |
| ***A61B 17/04*** | (2006.01) |
| ***A61F 2/40*** | (2006.01) |
| ***A61L 27/36*** | (2006.01) |
| ***B30B 1/20*** | (2006.01) |

(52) U.S. Cl.

CPC ..... *A61F 2/0811* (2013.01); *A61F 2220/0075* (2013.01)

(58) Field of Classification Search

CPC . B30B 1/20; B30B 1/18; A61F 2/0811; A61F 2220/0075; A61F 2/40; A61F 2/08; A61F 2240/001; A61F 2002/087; A61L 27/3691; A61B 2017/00526; A61B 17/0401

See application file for complete search history.

(56) References Cited

U.S. PATENT DOCUMENTS

| | | | |
|---|---|---|---|
| 5,545,222 | A | 8/1996 | Bonutti |
| 6,309,405 | B1 | 10/2001 | Bonutti |
| 6,503,277 | B2 | 1/2003 | Bonutti |
| 6,630,153 | B2 | 10/2003 | Long et al. |
| 6,652,260 | B2 | 11/2003 | Nelson et al. |
| 6,776,938 | B2 | 8/2004 | Bonutti |
| 6,860,904 | B2 | 3/2005 | Bonutti |
| 7,189,245 | B2 | 3/2007 | Kaplan |
| 7,462,200 | B2 | 12/2008 | Bonutti |
| 8,617,181 | B2 | 12/2013 | Sabir et al. |

(Continued)

FOREIGN PATENT DOCUMENTS

| | | | |
|---|---|---|---|
| CN | 202168873 | U | 3/2012 |
| CN | 103767758 | B | 12/2015 |

(Continued)

OTHER PUBLICATIONS

English translate (KR102201140B1), retrieved date Jun. 17, 2026.*

(Continued)

*Primary Examiner* — Mohammed S. Alawadi

(74) *Attorney, Agent, or Firm* — Carlson, Gaskey & Olds, P.C.

(57) ABSTRACT

This disclosure details compression systems and corresponding methods. An example system may include a first press component defining a cavity configured to receive a graft and a surgical implant. In the example, the first press component includes at least one slot configured to facilitate routing of suture in and out of the cavity. The example system further includes a second press component including a projection insertable into the cavity.

14 Claims, 7 Drawing Sheets

(56) References Cited

U.S. PATENT DOCUMENTS

| | | | |
|---|---|---|---|
| 8,974,535 B2 | 3/2015 | Antonyshyn et al. | |
| 9,615,922 B2 | 4/2017 | Munnelly et al. | |
| 9,616,152 B2 | 4/2017 | Samaniego et al. | |
| 9,752,112 B2 | 9/2017 | Watanabe et al. | |
| 2002/0025358 A1 | 2/2002 | Nelson et al. | |
| 2002/0040246 A1 | 4/2002 | Bonutti | |
| 2002/0106625 A1 | 8/2002 | Hung et al. | |
| 2004/0019132 A1 | 1/2004 | Long et al. | |
| 2012/0277152 A1 | 11/2012 | Ringeisen et al. | |
| 2012/0303058 A1 | 11/2012 | Huttunen et al. | |
| 2013/0134632 A1 | 5/2013 | Snedeker et al. | |
| 2017/0128215 A1 | 5/2017 | Denham | |
| 2017/0273795 A1* | 9/2017 | Neichel | A61F 2/28 |
| 2023/0113040 A1 | 4/2023 | Higgins et al. | |

FOREIGN PATENT DOCUMENTS

| | | | | |
|---|---|---|---|---|
| EP | 2528543 B1 | 10/2016 | | |
| EP | 3222253 A1 | 9/2017 | | |
| KR | 20100023420 A * | 3/2010 | A61F 2/186 | |
| KR | 102201140 B1 * | 1/2021 | A61L 27/3612 | |
| WO | 2020050514 A1 | 3/2020 | | |

OTHER PUBLICATIONS

English translate (KR20100023420A), retrieved date Jun. 17, 2026.*

Colbath G, Murray A, Siatkowski S, Pate T, Krussig M, Pill S, Hawkins R, Tokish J, Mercuri J, Autograft long head biceps tendon can be used as a scaffold for biologically augmenting rotator cuff repairs., Arthroscopy: The Journal of Arthroscopic and Related Surgery (2021), doi: https://doi.org/10.1016/j.arthro.2021.05.064.

Brooks, Jennifer, Autograft tissue compression system for CuffMend rotator cuff augmentation, Arthrex, Jan. 24, 2023.

International Search Report and Written Opinion for PCT/US2022/44197 dated Jan. 3, 2023.

V. Mueller AU13855—McKesson medical-surgical. V. Mueller AU13855—McKesson Medical-Surgical. (n.d.). https://mms.mckesson.com/product/922115/V-Mueller-AU13855.

Univers revers modular glenoid system, Arthrex.

Partial Search Report for International Application No. PCT/US2024/058322.

International Preliminary Report on Patentability for International Application No. PCT/US2024/058322 issued on Jun. 2, 2026.

* cited by examiner

COMPRESSION SYSTEM CONFIGURED TO EMBED GRAFT INTO SURGICAL IMPLANT AND CORRESPONDING METHOD

BACKGROUND

To re-establish stability within a shoulder joint after injury, for example, autograft tissue can be employed to span the humerus and the glenoid cavity of the scapula and repair the rotator cuff. Allograft tissue and synthetic grafts are alternate options.

SUMMARY

This disclosure details compression systems and corresponding methods. An example compression system is configured to embed at least a portion of a graft, such as autograft, allograft, or a synthetic graft, into a surgical implant, such as suture or mesh. The combined construct, which is formed by embedding at least a portion of the graft into the surgical implant, is then used for a surgical repair or reconstruction procedure in a patient's body. This disclosure also relates to the method of embedding at least a portion of a graft into a surgical implant, as well as the method of performing a surgical procedure including one or more steps associated with the graft, surgical implant, and/or the combined construct.

The systems and methods of this disclosure permit a user to readily create a construct including a surgical implant and a graft. The construct promotes healing following a surgical procedure, such as a soft tissue repair. These and other benefits will be appreciated by the below description.

In some aspects, the techniques described herein relate to a system, including: a first press component defining a cavity configured to receive a graft and a surgical implant, wherein the first press component includes at least one slot configured to facilitate routing of suture in and out of the cavity; and a second press component including a projection insertable into the cavity.

In some aspects, the techniques described herein relate to a surgical method, including: placing a surgical implant into a cavity of a first press component; placing a graft into the cavity of the first press component; and embedding at least a portion of the graft into the surgical implant by applying a force to the graft by moving a second press component relative to the first press component, wherein the second press component includes a projection insertable into the cavity of the first press component.

BRIEF DESCRIPTION OF THE DRAWINGS

In FIG. 6, suture is within cavities of the first press component, and the surgical device is not interfaced with the first press component.

In FIG. 7, suture is within the cavities of the first press component, and the surgical device is interfaced with the first press component.

In FIG. 9, the first and second press components are shown side-by-side, with the first press component shown from a top perspective, and the second press component shown from a bottom perspective.

In FIG. 12, at least a portion of the graft is embedded into the surgical device.

DETAILED DESCRIPTION

Figure 1:
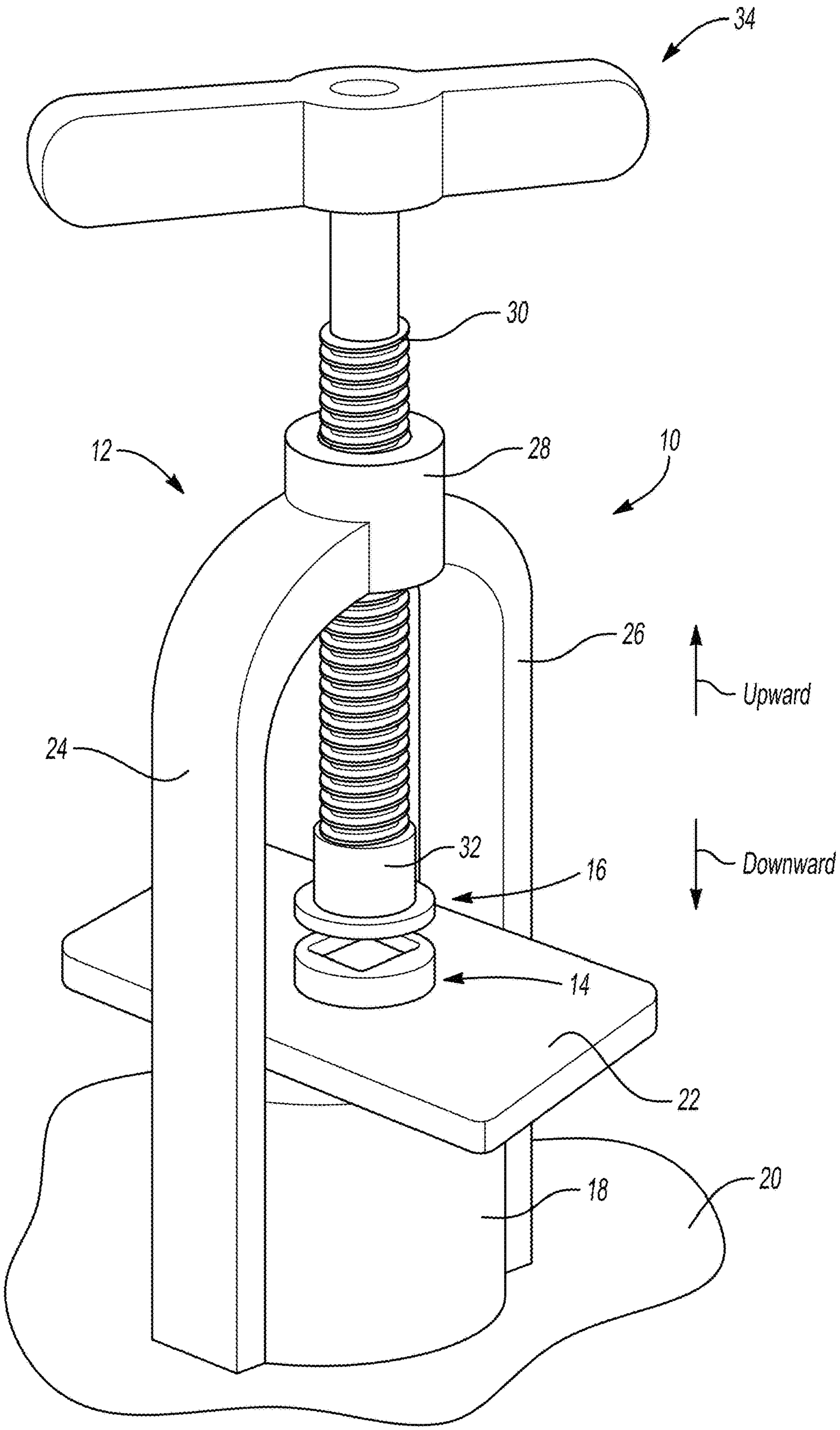
FIG. 1 is a perspective view of an example compression system.

This disclosure details compression systems and corresponding methods. With reference to the drawings, FIG. 1 illustrates an example surgical system 10 ("system 10"). The system 10 may be referred to as a compression system. As shown in FIG. 1, the system 10 includes a press 12, a first press component 14, and a second press component 16. The press 12, in this example, may be manually operated and is configured to move the first and second press components 14, 16 relative to one another to compress, and thereby flatten and change one or more dimensions of a graft, which may be allograft, autograft, or a synthetic graft. As will be discussed below, the press 12 and the first and second press components 14, 16 are used to embed at least a portion of the graft into a surgical implant, such as suture or mesh. The term "embed" is used in this disclosure to mean fix in a surrounding mass. So, the first and second press components 14, 16 are used to fix at least a portion of a graft into a surgical implant.

The press 12 may be manually operated in this example. However, one or more components of the press 12 could be controlled using an electromechanical and/or hydraulic device, such as an actuator. Further, while one example press 12 is shown in FIG. 1, it should be understood that this disclosure extends to other devices configured to apply forces resulting in relative movement of the first and second press components 14, 16, including clamps, vises, levers, etc.

In this example, the press 12 includes a stand 18 configured to rest on a worktop 20 or other surface, such as a table. The press 12 also includes a base 22 mounted above the stand 18. With reference to directional terms, the "upward" and "downward" directions are labeled in FIG. 1 and are used with reference to the normal operating orientation of the press 12, the first press component 14, and the second press component 16. The first press component 14 may be mounted to the base 22. In this example, the first press component 14 and base 22 are configured to remain stationary during use of the press 12.

The press 12 further includes a pair of support arms 24, 26 projecting from opposite sides of the stand 18 and converging on a nut 28 spaced upward of the base 22. The nut 28 may be configured to remain stationary during use of the press 12. The nut 28 includes a threaded through-bore which receives a shaft 30. The shaft 30 may be at least partially threaded, and the threads of the shaft 30 cooperate with threads of the nut 28 such that rotation of the shaft 30 results in movement of the shaft 30 in either the upward or downward direction relative to the nut 28 depending on the direction of rotation.

Below the nut 28, the shaft 30 may be connected to the second press component 16 via a connector 32, which may be mounted adjacent an end of the shaft 30. The connector 32 may be configured to transmit vertical movement of the shaft 30 to the second press component 16 without transmitting rotational movement of the shaft 30 to the second press component 16. The connector 32 can be integrally formed with the second press component 16. Above the nut 28, the shaft 30 may be connected to a handle 34. The handle 34 permits a user, such as a surgeon or surgical assistant, to apply a rotational force to the shaft 30 via the handle 34. Ultimately, the user is able to selectively raise and lower the second press component 16 relative to the first press component 14 by rotating the handle 34. In other embodiments, the second press component 16 is not attached to the connector 32, but is rather formed separately from the connector 32. In that embodiment, the connector 32 may still be able to contact the second press component 16 and to apply force to the second press component 16 to apply force to objects between the first and second press components 14, 16.

Figure 2:
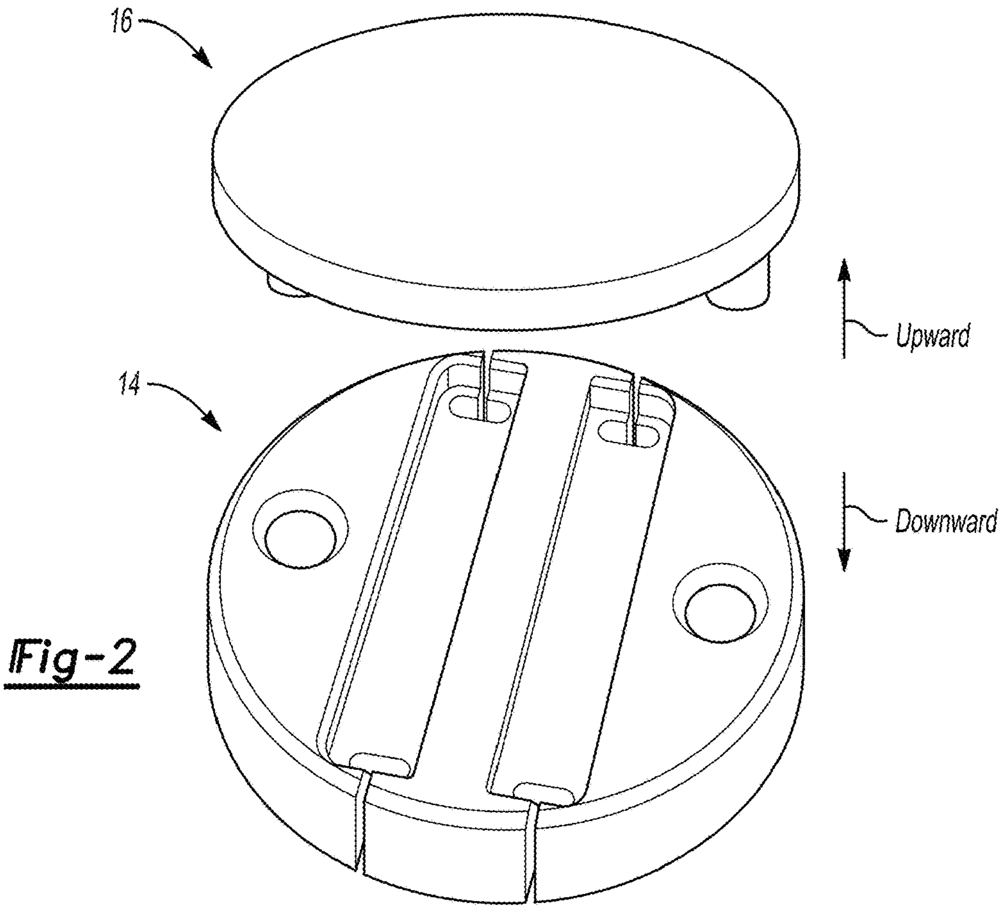
FIG. 2 is an exploded view of a first press component and a second press component.

Example first and second press components 14, 16 are shown relative to one another in an exploded view in FIG. 2. The first and second press components 14, 16 may be referred to as female and male components, respectively. The term "component" as used in the context of the first and second press components 14, 16 is not intended to be a nonce term or placeholder serving as a substitute for "means."

Figure 3:
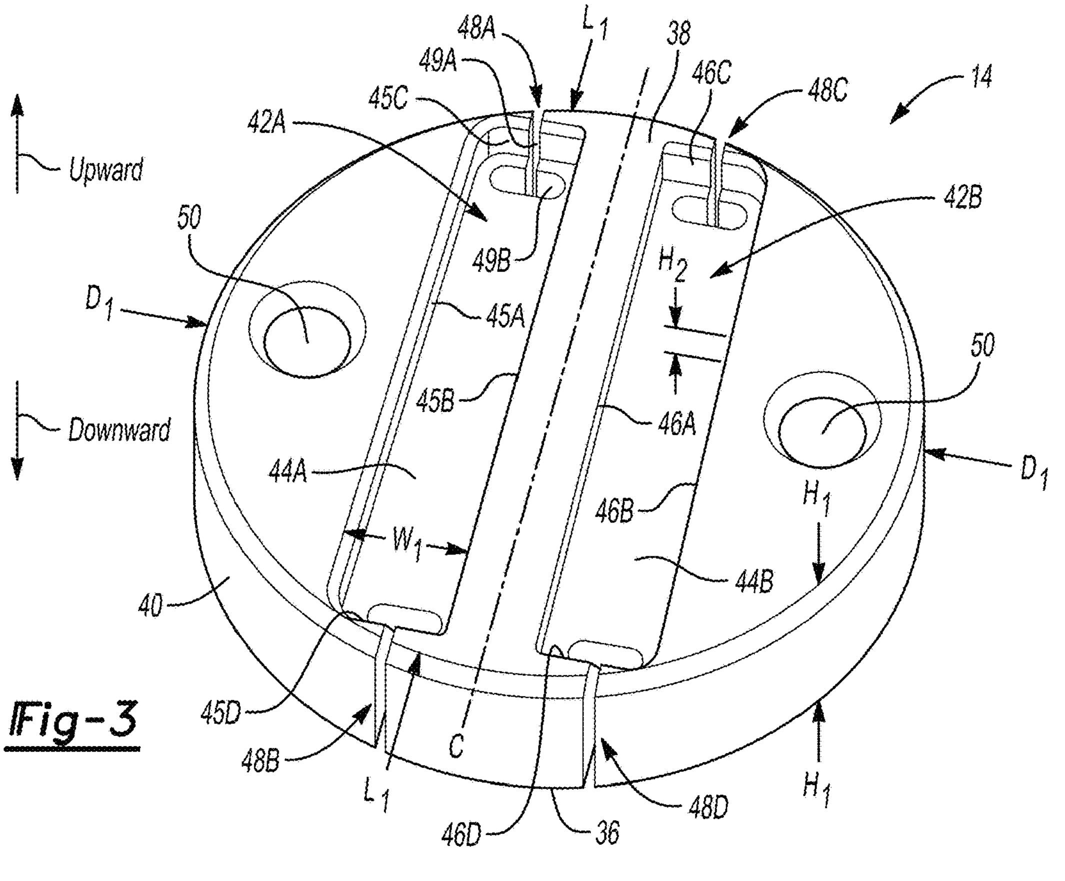
FIG. 3 is a top perspective view of the first press component.

FIG. 3 illustrates additional detail of the first press component 14. The first press component 14 exhibits a height $H_1$ between a bottom surface 36 and a top surface 38. The bottom surface 36 may be configured to rest upon, or be fixed to, the base 22. The bottom surface 36 may include one or more attachment features configured to facilitate an attachment of the first press component 14 to the base 22. In this example, the first press component 14 exhibits a circular perimeter 40, which may be referred to as a perimeter wall. The perimeter 40 provides the first press component 14 with a diameter $D_1$. The perimeter 40 is not limited to being circular in shape.

The first press component 14 includes a first cavity 42A and a second cavity 42B. While two cavities 42A, 42B are shown in the embodiment of FIG. 3, the first press component 14 could include one or more cavities.

The first and second cavities 42A, 42B are defined by the first press component 14. Specifically, in this example, the first and second cavities 42A, 42B are recessed downward, toward the bottom surface 36, from the top surface 38. The majority of a bottom surface of the cavities 42A, 42B are defined and bound by respective, upward-facing forming surfaces 44A, 44B. The forming surfaces 44A, 44B are recessed by a height $H_2$, which is less than $H_1$, from the top surface 38. Cavity 42A is bound by side walls 45A, 45B and end walls 45C, 45D, in this example, which provide the cavity 42A with a rectangular shape having a length $L_1$ greater than a width $W_1$. Cavity 42B is bound by side walls 46A, 46B and end walls 46C, 46D, in this example, which provide the cavity 42B with a rectangular shape having the length $L_1$ and the width $W_1$. Other cavity shapes come within the scope of this disclosure. The walls 45A-45D, 46A-46D exhibit the height $H_2$ and may be oriented at 90° angles relative to adjacent walls. Further, there may be rounded corners to provide smooth transitions between the walls 45A-45D, 46A-46D.

The first and second cavities 42A, 42B exhibit substantially the same size and shape, and in this example are substantial mirror images of one another about a centerline C of the first press component 14. The first and second cavities 42A, 42B extend substantially parallel to one another, and further extend substantially parallel to the centerline C.

The first press component 14 includes two guide openings 50 on opposite sides of the cavities 42A, 42B, and on opposite sides of the centerline C. The guide openings 50 may be through-holes extending from the top surface 38 through to the bottom surface 36. The guide openings 50 are configured to receive guide pins of the second press component 16 to facilitate alignment of the first and second press components 14, 16 during use of the press 12.

The first press component 14 further includes four slots 48A-48D, each arranged adjacent a corresponding end wall of one of the cavities 42A, 42B. As will be explained below, the slots 48A-48D facilitate routing of suture in and out of the cavities 42A, 42B. With reference to one of the slots 48A, slot 48A includes a first section 49A leading from the cavity 42A, through wall 45C, and is open to the perimeter 40 of the first press component 14. The slot 48A further includes a second section 49B within the cavity 42A and extending substantially perpendicular to the first section 49A. The second section 49B extends between side walls 45A, 45B and exhibits a dimension less than the width $W_1$. The first and second sections 49A, 49B extend through the entire height of the first press component 14. While only the slot 48A has been described, the remaining slots 48B-48D are configured similarly. Slots 48A-48D are not required in all examples. When slots 48A-48D are present, the second press component 16 could also include corresponding slots, sized and shaped to vertically overlap the slots 48A-48D of the first press component 14.

Figure 4:
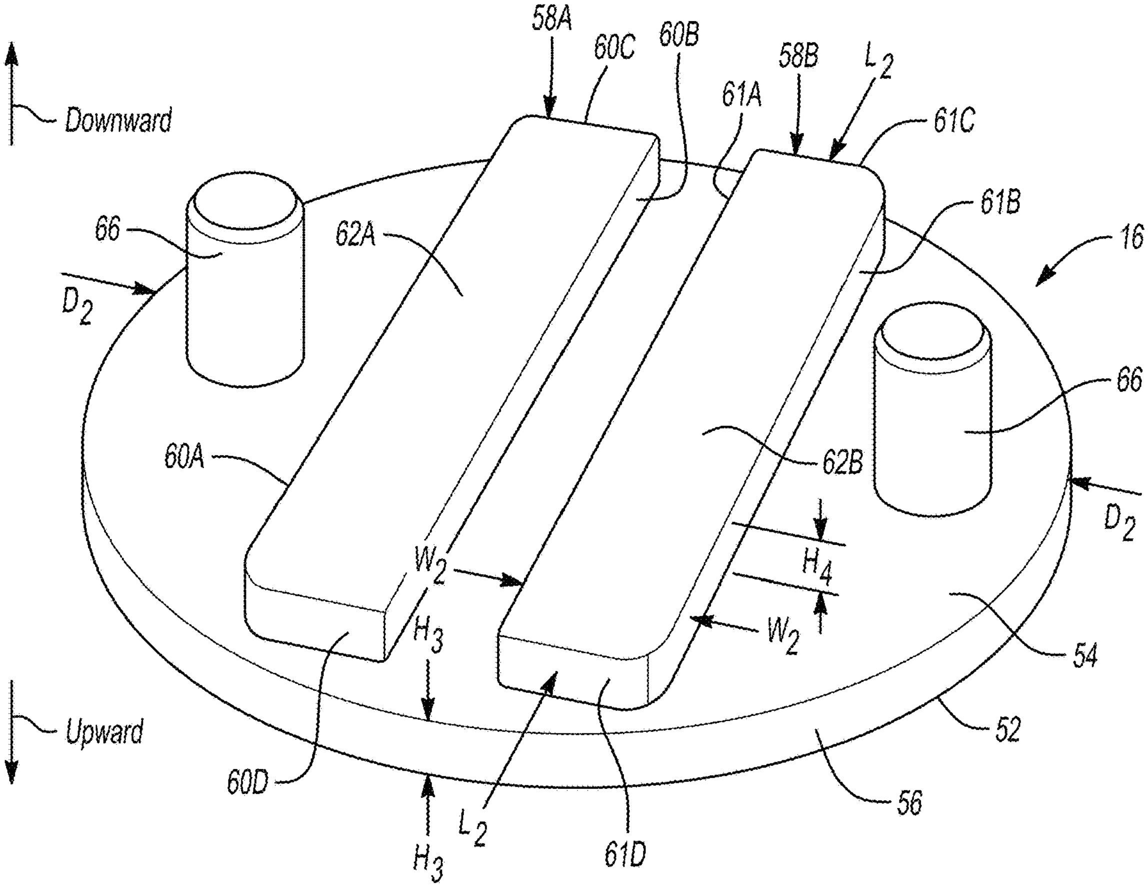
FIG. 4 is a bottom perspective view of the second press component.

Additional detail of the second press component 16 is illustrated in FIG. 4. The second press component 16 exhibits a height $H_3$ between a top surface 52 and a bottom surface 54. The top surface 52 may be configured to contact, or to attach to, the connector 32. The top surface 52 may include one or more attachment features configured to facilitate attachment to the connector 32. In this example, the second press component 16 exhibits a circular perimeter 56 defining a diameter $D_2$, which may be substantially equal to diameter $D_1$. The perimeter 56 could exhibit other shapes, however.

The second press component 16, in this example, includes one or more projections projecting downward from the bottom surface 54. In this example, the second press component 16 includes two projections 58A, 58B projecting downward from the bottom surface 54. The projection 58A is bound by side walls 60A, 60B and end walls 60C, 60D. The projection 58B is bound by side walls 61A, 61B and end walls 61C, 61D. The walls 60A-60D, 61A-61D each exhibit a height $H_4$ and provide the projections 58A, 58B with a rectangular shape exhibiting a length $L_2$ and a width $W_2$. The walls 60A-60D, 61A-61D may be arranged at 90° relative to one another, with rounded corners. In this example, the height $H_4$ is substantially equal to the height $H_2$. In a particular example, the height $H_4$ is slightly greater than the height $H_2$. Further, in this example, the length $L_2$ and width $W_2$ are substantially equal to, but slightly less than, the corresponding length $L_1$ and width $W_1$ of the cavities 42A, 42B such that a corresponding one of the projections 58A, 58B fits into a corresponding cavity 42A, 42B to provide a sliding fit between the respective cavities 42A, 42B and projections 58A, 58B. The projections 58A, 58B each exhibit a main downward-facing forming surface 62A, 62B, which is spaced-apart from the bottom surface 54 by height $H_4$, and exhibits the length $L_2$ and the width $W_2$.

In order to facilitate alignment of the first and second press components 14, 16, and to further facilitate a sliding fit between the cavities 42A, 42B and the projections 58A, 58B, the second press component 16 includes guide pins 66 on opposite sides of the projections 58A, 58B. The guide pins 66 are configured to align with and be received in the guide openings 50 of the first press component 14. The guide openings 50 and guide pins 66 are dimensioned so as to permit a sliding fit between the guide openings 50 and guide pins 66.

Figure 5:
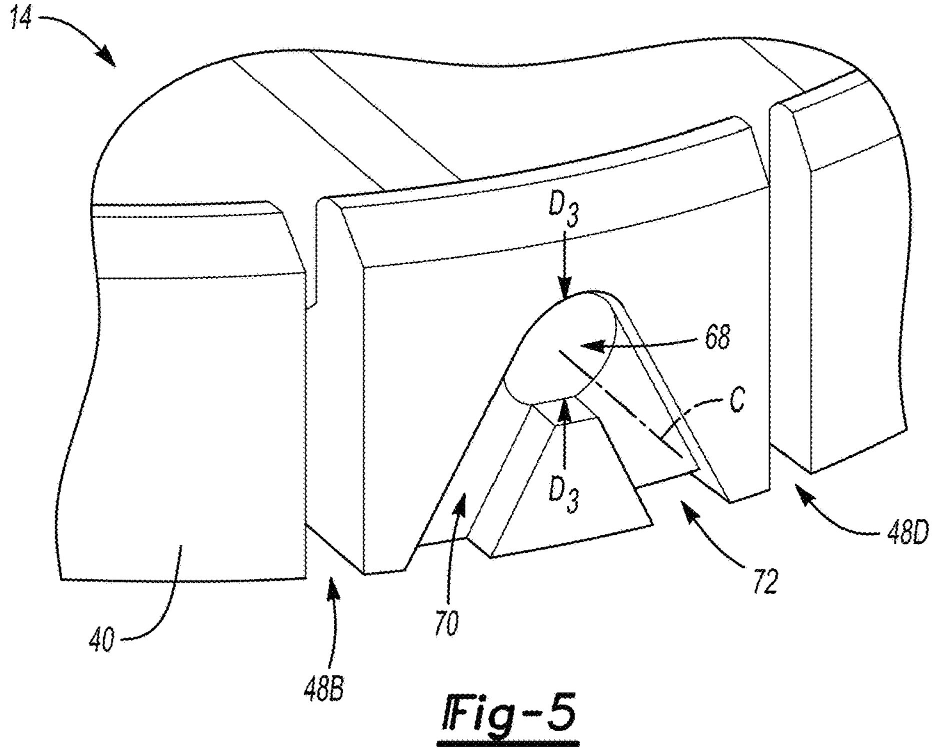
FIG. 5 is a close-up view of a portion of the first press component that is configured to interface with a surgical device.

An aspect of this disclosure relates to interfacing a surgical device relative to the first press component 14, and routing suture carried by that surgical device into the cavities 42A, 42B. With reference to FIG. 5, in an example, an opening 68 is formed in the perimeter 40 of the first press component 14 between slots 48B, 48D. The center of the opening 68 lies on the centerline C in this example. The opening 68 may not be a through-opening, but rather may project into the perimeter 40 in a direction parallel to the centerline C. The opening 68 may be substantially circular in cross-section and in this example exhibits a diameter $D_3$, which is slightly greater than a distal end section of a surgical device to be interfaced with the first press component 14. The opening 68 exhibits a depth, from the perimeter wall 40 moving toward the center of the first press component 14, sufficient to support the surgical device. The opening 68 may be configured to support a surgical device that includes a rigid implant or a soft implant.

The perimeter 40 of the first press component 14 includes a first groove 70 extending downwardly from the opening 68 and inclined toward the slot 48B, and, on an opposite side of the opening 68, the perimeter 40 includes a second groove 72 extending downwardly from the opening 68 and inclined toward and the slot 48D. The first and second grooves 70, 72 facilitate routing of suture relative to the cavities 42A, 42B. The first and second grooves 70, 72 may be configured such that suture can be routed into the cavities 42A, 42B without interfering with how the bottom surface 36 contacts the base 22.

Figure 6:
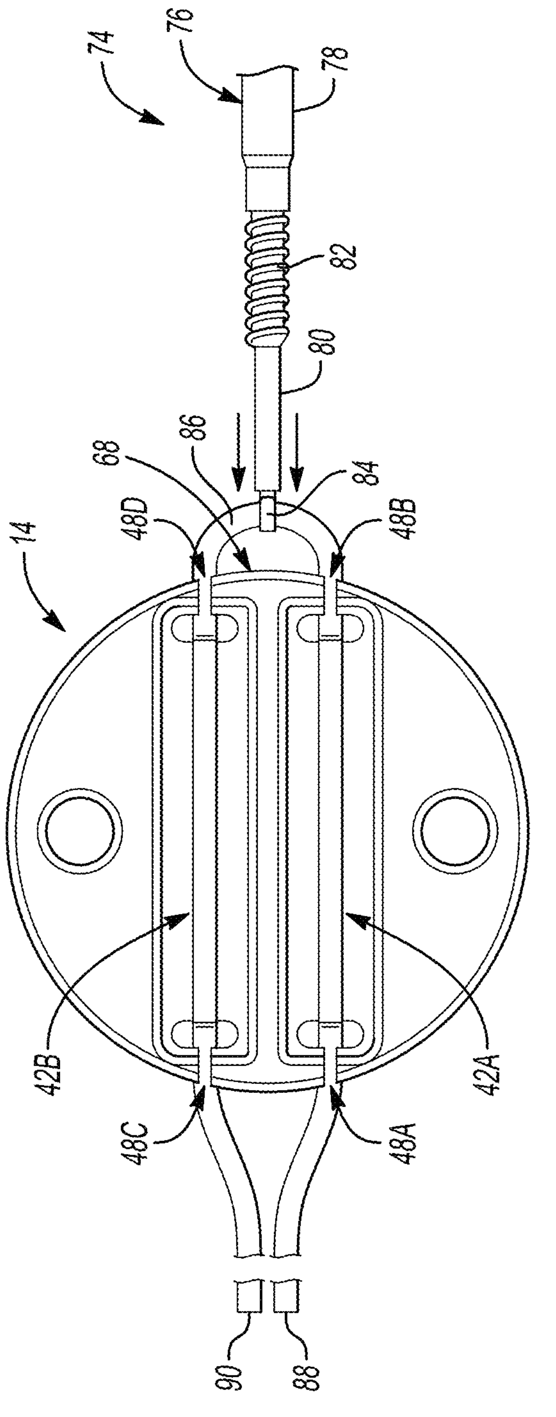
FIG. 6 is a top view of the first press component relative to a surgical device and suture.

FIG. 6 illustrates a portion of a surgical device 74 relative to the first press component 14. The surgical device 74 is exemplary only. Other surgical devices can interface with the first press component 14.

In the example of FIG. 6, the surgical device 74 includes a driver 76 which includes an outer shaft 78 and an inner shaft 80. The outer shaft 78 may be cannulated for receiving inner shaft 80. The driver 76 may be pre-loaded with an interference device 82. The interference device 82 can be a screw or an interference plug. The interference device 82 comprises a cannula, which can be hex-shaped, for accommodating the correspondingly-shaped inner shaft 80.

A structure 84 forming an eyelet may be arranged at the distal end of driver 76. The structure 84 may be releasably attached to the driver 76. The structure 84 and the inner shaft 80 exhibit a diameter less than diameter $D_3$ so the structure 84 and inner shaft 80 can fit into the opening 68. Suture 86 may be carried by the surgical device 74. The suture 86 freely slides through the eyelet of the structure 84.

As shown in FIG. 6, with the surgical device 74 spaced-apart from the first press component 14, the slots 48A-48D permit one to readily route the suture 86 through the first and second cavities 42A, 42B. In particular, the suture 86, which is a strand having free ends 88, 90, is routed such that free end 88 passes through slot 48B, into cavity 42A, and exits cavity 42A via slot 48A. Further, free end 90 passes through slot 48D, into cavity 42B, and exits cavity 42B via slot 48C.

The suture 86 may be a strand of suture tape, such as FiberTape®. FiberTape® is a suture product marketed and sold by Arthrex, Inc. However, other types of suture come within the scope of this disclosure. In the example where the suture 86 is FiberTape®, the suture 86 lays relatively flat on the forming surfaces 44A, 44B of cavities 42A, 42B. The suture 86 may be a modified, more porous, version of FiberTape® in an example.

Figure 7:
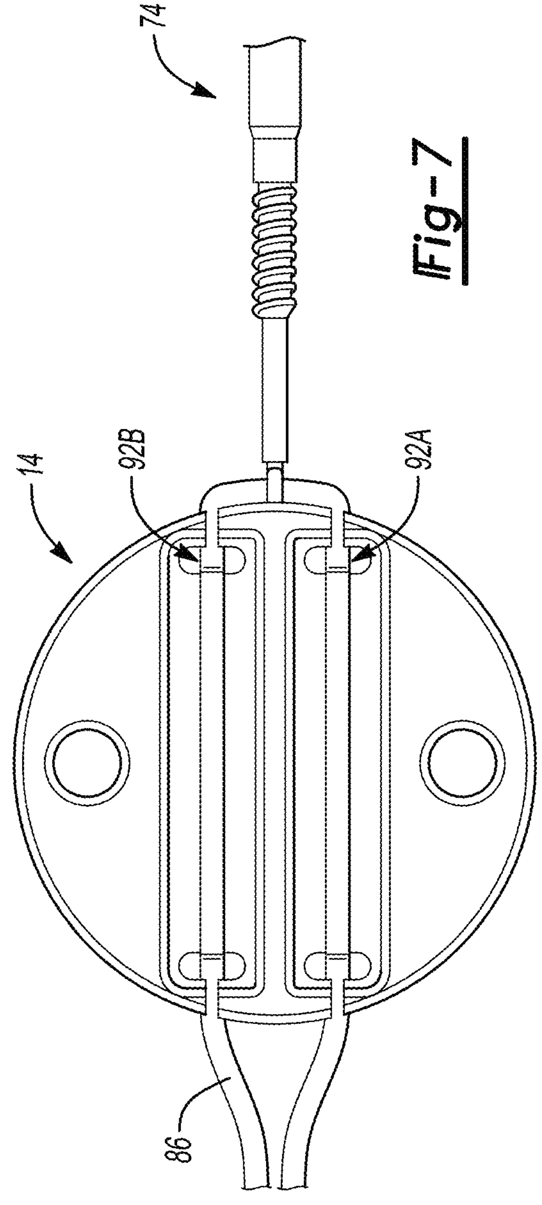
FIG. 7 is a top view of the first press component relative to the surgical device and suture.

As shown in FIG. 7, the surgical device 74 is interfaced with the first press component 14. In FIG. 7, the structure 84 is fully within the opening 68, and the inner shaft 80 is partially within the opening 68. The suture 86 is routed through first and second grooves 70, 72 and the first and second ends 88, 90 may be pulled taught.

Figure 8:
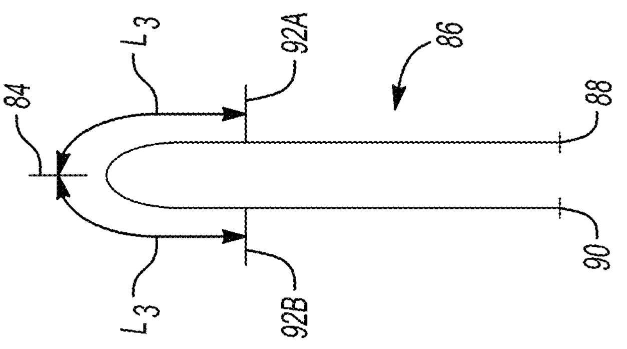
FIG. 8 schematically illustrates the suture of FIGS. 6 and 7.

In this respect, the opening 68 and the first and second grooves 70, 72 may be sized and shaped such that a length $L_3$ of the suture 86 between the structure 84 and a point 92A, 92B where the suture 86 first enters one of the cavities 42A, 42B is substantially equal to a length of the interference device 82. In another embodiment the length $L_3$ is substantially equal to a length of the interference device 82 plus the length of the structure 84. In this way, a graft can be embedded into the portion of the suture 86 that is intended to be outside a bone hole. The length $L_3$ is schematically represented in FIG. 8. In an example, the length $L_3$ is within a range of 18-20 mm. In a specific example, the length $L_3$ is 19 mm. While specific dimensions have been mentioned, this disclosure extends to other dimensions.

Figure 9:
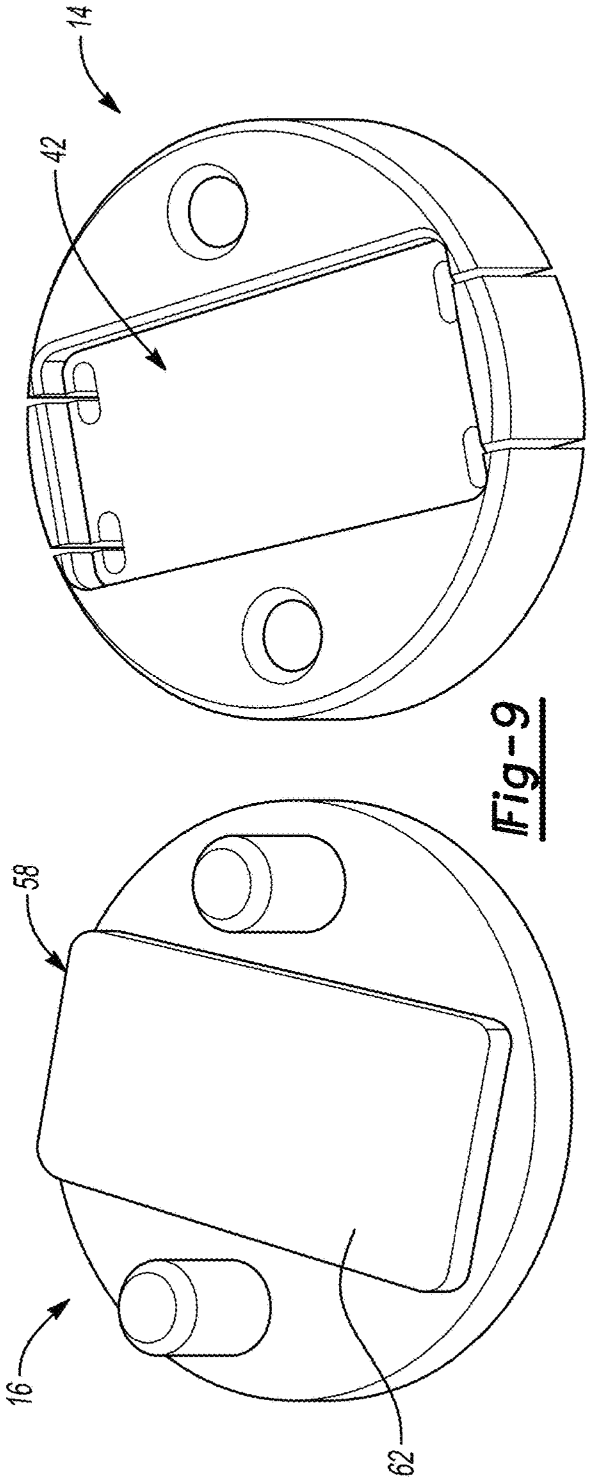
FIG. 9 illustrates another embodiment of the first press component and the second press component in which the first press component includes a single cavity and the second press component includes a single projection.

FIG. 9 illustrates an embodiment of the first press component 14 and the second press component 16, with the first press component 14 including a single, rectangular-shaped cavity 42, and the second press component 16 including a single, rectangular-shaped projection 58. The first and second press components 14, 16 may otherwise be substantially similar to the above-discussed first and second press components 14, 16. Notably, the first press component 14 of FIG. 9 includes slots 48A-48D in respective corners of the single cavity 42. The slots 48A-48D are not required in all examples. The first press component 14 of FIG. 9 may also optionally include an opening, such as opening 68, configured to interface with a surgical device, and grooves, such as grooves 70, 72, to facilitate routing of suture.

Figure 10:
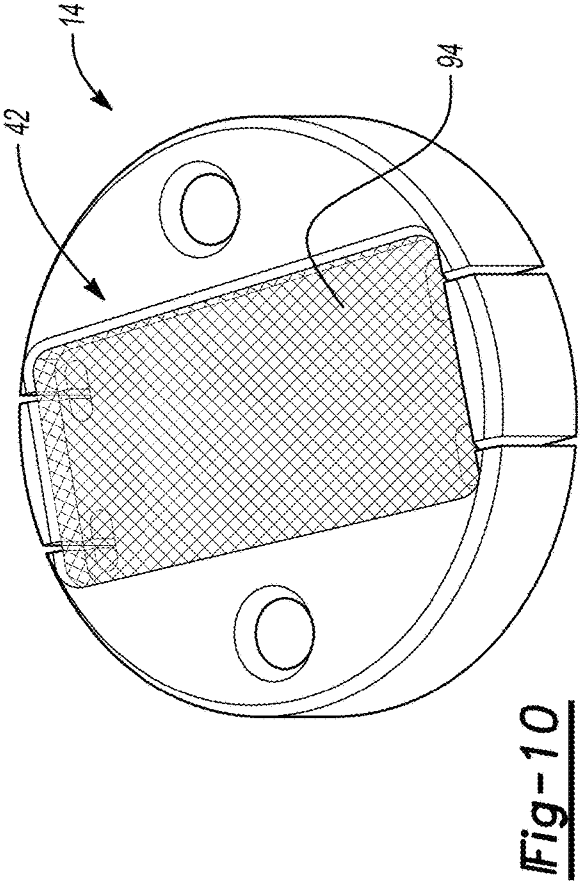
FIG. 10 illustrates mesh within a cavity of the first press component of FIG. 9.

Because the single cavity 42 of FIG. 9 may be relatively larger than cavities 42A, 42B, the embodiment of FIG. 9 may be particularly suited to receiving mesh 94, as shown in FIG. 10. The mesh 94 may be a flat, flexible weave and may be made of polypropylene or polyester, as examples. While the single cavity 42 receives mesh 94, the relatively narrower cavities 42A, 42B, on the other hand, may be particularly suited to receive suture 86, as shown in FIGS. 6 and 7, for example. The cavities 42, 42A, 42B, however, are not limited to receiving these particular surgical implants. For example, the cavities 42A, 42B could receive mesh, and the single cavity 42 could receive suture. The cavities 42, 42A, 42B could receive both suture and mesh simultaneously, such as by receiving mesh that includes suture. The cavities 42, 42A, 42B could receive other types of surgical implants.

In this disclosure, at least one of the first press component 14 and the second press component 16 may be made of at least a semi-transparent material such that a graft and surgical implant can be viewed through the first press component 14 and/or the second press component 16 while the press 12 is in use. In a further aspect of this disclosure, at least one of the first press component 14 and the second press component 16 may be formed of a transparent material. An example transparent material may be a clear polycarbonate material. Other transparent materials come within the scope of this disclosure. In a specific example, at least the second press component 16 may be made of transparent material. In an even more specific example, both the first and second press components 14, 16 are made of transparent material. By providing at least one of the first and second press components 14, 16 of at least semi-transparent, if not fully transparent material, the graft and surgical implant are visible through at least one of the first and second press components 14, 16. When both the first and second press components 14, 16 are made of semi-transparent or fully transparent material, the vertical dimension, or height, of the graft may be more readily visible. Regardless, a user of the press 12 can monitor the reaction of the graft as compressive forces are applied to the graft to determine if the graft has been embedded into the surgical implant as desired such that the user can cease use of the press 12.

An example method of use will now be described relative to FIGS. 11-14, and with continued reference to FIGS. 1-10. A surgeon may perform the method either partially or entirely. One or more steps of the method may be performed by another, such as a surgical assistant. The method may be performed either partially or entirely during an arthroscopic surgical procedure.

Initially, a graft is provided. The graft may be allograft, autograft, or a synthetic graft. When the graft is an autograft, tissue is harvested from a first location in a body of a patient. In an example, the first location is one of the latissimus dorsi, pectoralis major, and fascia lata. This disclosure extends to other harvesting locations.

Figures 11, 12:
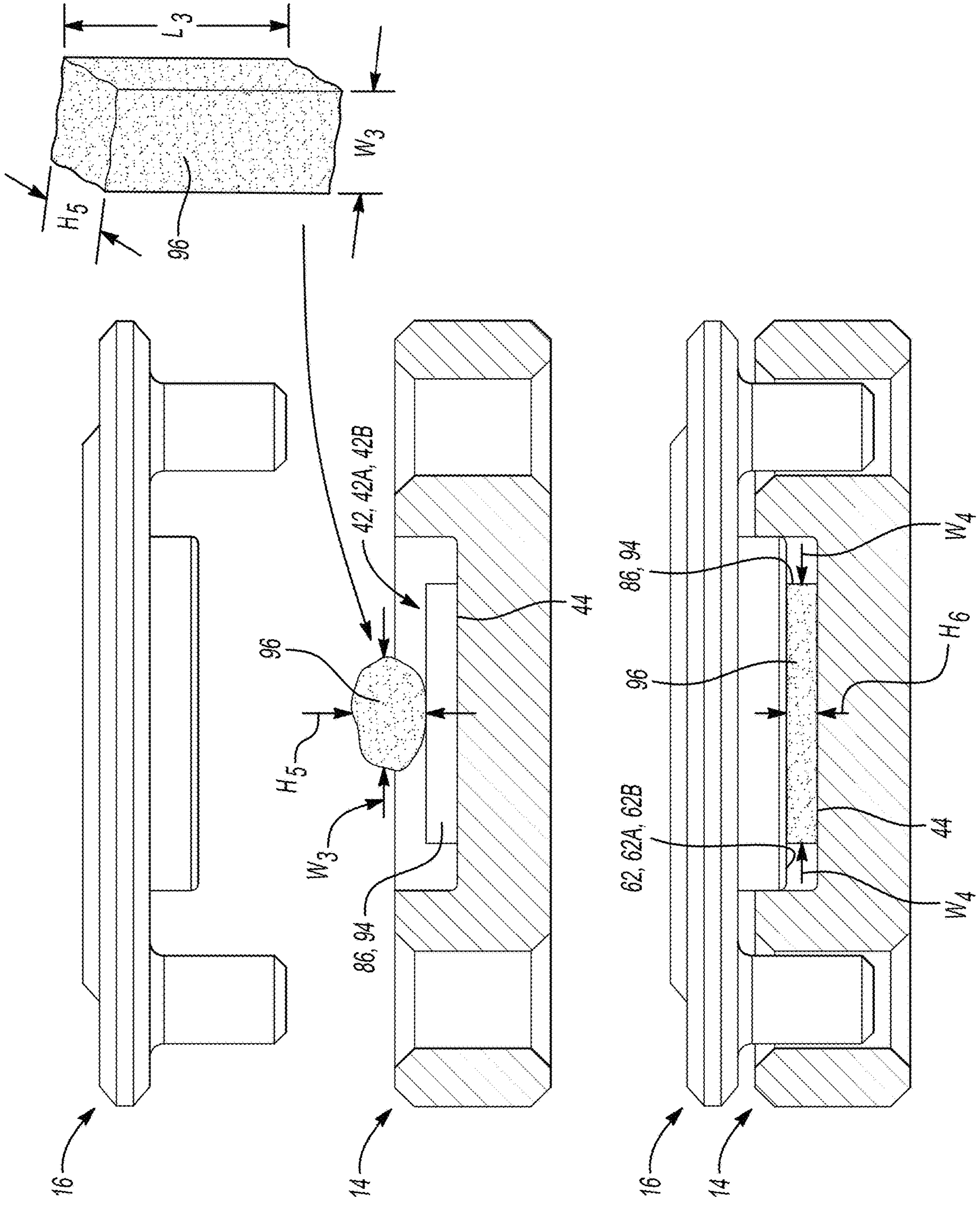
FIG. 11 is a cross-sectional view representative of the first press component spaced-apart from the second press component such that a graft and surgical device can be placed into the cavity of the first press component.
FIG. 12 is a cross-sectional view similar to FIG. 11, but with the projection of the second press component partially inserted into the cavity.

An example graft 96 is shown in FIG. 11. The graft 96 exhibits a length $L_3$, a width $W_3$, and a height $H_5$. While shown as a substantial rectangular cuboid, the graft 96 could exhibit another shape.

In this example, a surgical implant is arranged in the cavity. The surgical implant is represented in FIGS. 11 and 12 schematically, as the suture 86 or the mesh 94. The cavity is also represented schematically, as any of the cavities 42, 42A, or 42B. The graft 96 is situated at least partially in the cavity.

In FIG. 11, the second press component 16 is spaced-apart vertically upward of the first press component 14 to permit placement of the graft and surgical implant into the cavity of the first press component 14. In this example, the graft 96 is situated on top of the surgical implant within the cavity. The graft 96 could be situated below the surgical implant, however.

In one example, when the surgical implant is suture, FIG. 11 represents an arrangement of the surgical implant equivalent to what is shown in FIG. 7. In another example, when the surgical implant is mesh, FIG. 11 represents an arrangement of the surgical implant equivalent to what is shown in FIG. 10.

Once the graft and surgical implant are arranged relative to the cavity, the user may begin rotating the handle 34 to apply force to the second press component 16 such that the forming surface, representative of forming surfaces 62 (FIG. 9), 62A, and 62B, comes into contact with the graft 96, which causes the graft 96 to become compressed. Because of the porosity of the surgical implant, namely the mesh or suture, compressing the graft 96 causes at least a portion of the graft 96 to become embedded within the surgical implant. As shown in FIG. 12, the graft 96 exhibits a width $W_4$ greater than the width $W_3$ and a height $H_6$ less than the height $H_5$. The user may be able to view the changed dimensions of the graft 96 through one or both of the first and second press components 14, 16, which again may be semi-transparent or fully transparent.

Figure 13:
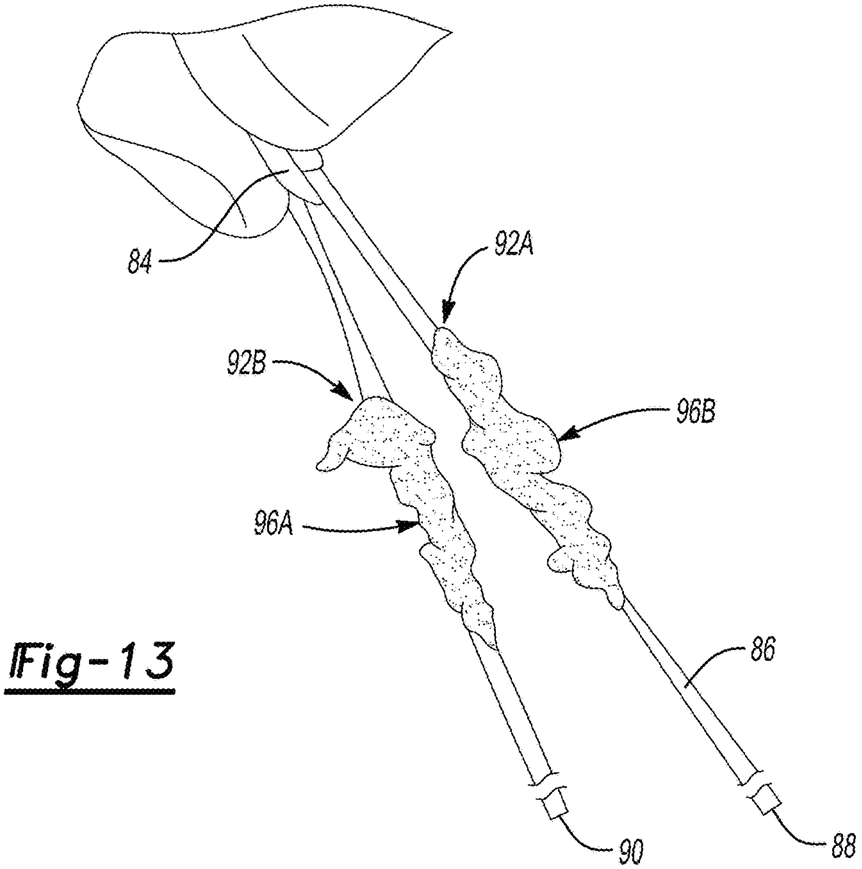
FIG. 13 is a perspective view of suture, with two grafts, each at least partially embedded into the suture.
Figure 14:
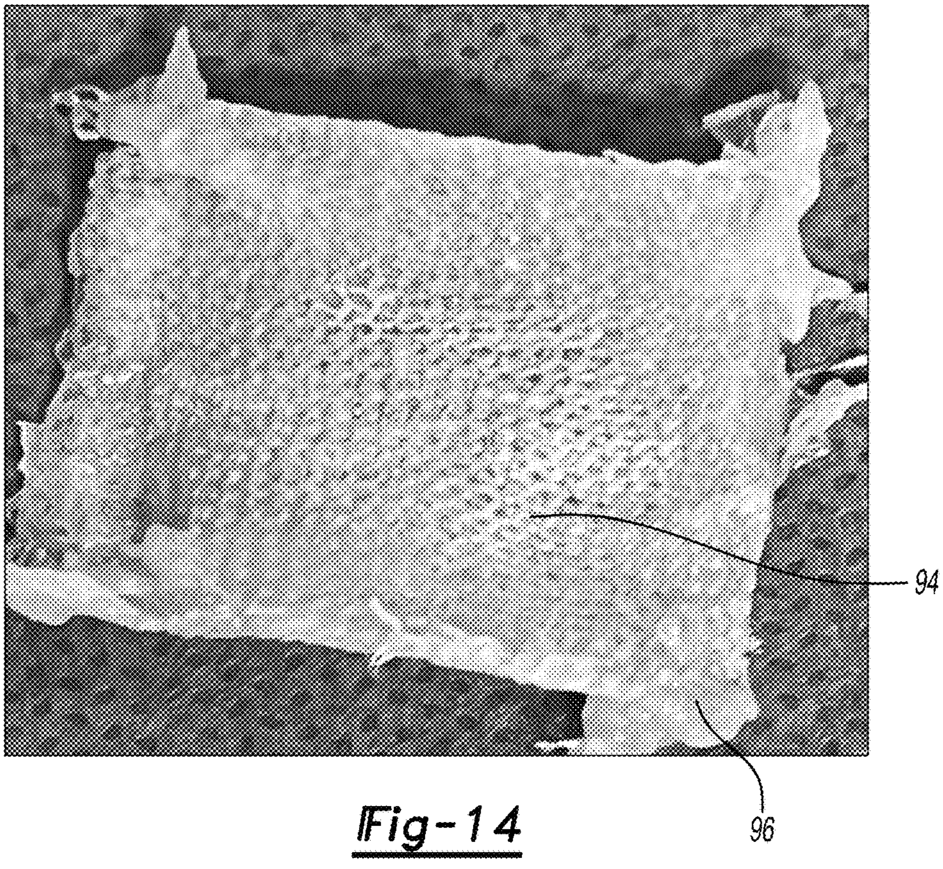
FIG. 14 is a perspective view of a mesh, with a graft at least partially embedded into the mesh.

FIG. 13 is representative of two grafts 96A, 96B embedded, at least partially, into the suture 86. As shown, the grafts 96A, 96B are not embedded into the suture between points 92A, 92B and the structure 84. The grafts 96A, 96B are on an opposite side of points 92A, 92B than the structure 84. If the grafts 96A, 96B extend to a same side of points 92A, 92B as the structure 84, the grafts 96A, 96B can be trimmed. FIG. 14 is representative of a graft 96 embedded at least partially into mesh 94. In both instances, the grafts 96A, 96B, 96 can be trimmed to a desired size or shape.

Embedding the graft(s) at least partially into the surgical implant promotes growth and healing. The method may also include soaking the surgical implant with platelet-rich-plasma (PRP), either before or after embedding the graft into the surgical implant, to further promote growth and healing.

The constructs including the surgical implant and graft may be used to provide a partial or full replacement for a torn rotator cuff. This disclosure is not limited to use in rotator cuff repairs/reconstructions, however, and extends to uses in other repair or reconstruction techniques, including techniques involving repair or reconstruction of the hand, wrist, toe, Achilles tendon, Peroneal/Tibial tendon, among others. As another example, the constructs may be used in a superior capsular reinforcement technique.

It should be understood that directional terms such as top, bottom, upward, downward, etc., are used herein consistent with their art-accepted meaning and with reference to the normal operational orientation of the relevant components. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A system, comprising:

a first press component defining a cavity configured to receive a graft and a surgical implant, wherein the first press component includes at least one slot configured to facilitate routing of suture in and out of the cavity, wherein the at least one slot includes a first section open to an outer perimeter of the first press component, and wherein the at least one slot includes a second section intersecting with the first section; and a second press component including a projection insertable into the cavity.

2. The system as recited in claim 1, wherein the second section is oriented substantially perpendicular to the first section.

3. The system as recited in claim 1, wherein the at least one slot is one of a plurality of slots of the first press component.

4. The system as recited in claim 1, wherein:

the cavity of the first press component is a first cavity, the first press component includes a second cavity, the projection of the second press component is a first projection, and the second press component includes a second projection insertable into the second cavity.

5. The system as recited in claim 4, wherein:

the first and second cavities are sized and shaped substantially similar to one another, and the first and second projections are sized and shaped substantially similar to one another.

6. The system as recited in claim 4, wherein the first and second cavities extend substantially parallel to one another and are arranged on opposite sides of a centerline of the first press component.

7. The system as recited in claim 6, wherein:

the at least one slot is one of a plurality of slots of the first press component, a first one of the slots is arranged adjacent a first end of the first cavity, a second one of the slots is arranged adjacent a second end of the first cavity opposite the first end, a third one of the slots is arranged adjacent a first end of the second cavity, and a fourth one of the slots is arranged adjacent a second end of the second cavity opposite the first end.

8. The system as recited in claim 1, wherein at least one of the first and second press components is made of a transparent or semi-transparent material.

9. The system as recited in claim 1, wherein the at least one of the first and second press components is made of a transparent material.

10. The system as recited in claim 1, further comprising a press configured to move the first press component and second press component toward one another to embed at least a portion of the graft into the surgical implant.

11. The system as recited in claim 10, wherein the press includes a base and a shaft moveable relative to the base.

12. A system, comprising:

a first press component defining a cavity configured to receive a graft and a surgical implant, wherein the first press component includes at least one slot configured to facilitate routing of suture in and out of the cavity; and a second press component including a projection insertable into the cavity, wherein the cavity of the first press component is a first cavity, wherein the first press component includes a second cavity, wherein the projection of the second press component is a first projection, and wherein the second press component includes a second projection insertable into the second cavity, wherein the first and second cavities extend substantially parallel to one another and are arranged on opposite sides of a centerline of the first press component, wherein the at least one slot is one of a plurality of slots of the first press component, wherein a first one of the slots is arranged adjacent a first end of the first cavity, wherein a second one of the slots is arranged adjacent a second end of the first cavity opposite the first end, wherein a third one of the slots is arranged adjacent a first end of the second cavity, wherein a fourth one of the slots is arranged adjacent a second end of the second cavity opposite the first end, wherein a perimeter wall of the first press component includes an opening configured to receive a portion of a surgical device, wherein the perimeter wall of the first press component includes a first groove extending from the opening toward the first slot, wherein the perimeter wall of the first press component includes a second groove extending from the opening toward the third slot, wherein the suture is carried by the surgical device, and wherein the first press component is configured such that the suture is able to be routed into the first and second cavities via the first and second grooves and the first and third slots.

13. The system as recited in claim 12, wherein the first press component is configured such that the suture is able to be routed out of the first and second cavities via the second and fourth slots.

14. The system as recited in claim 12, wherein a length of the first and second grooves is substantially equal to a length of an interference device of the surgical device.

* * * * *